(12) United States Patent
Kachikian et al.

(10) Patent No.: US 11,738,163 B2
(45) Date of Patent: Aug. 29, 2023

(54) GAS DETECTOR FOR A FACE MASK

(71) Applicant: De Nova Technology, Placerville, CA (US)

(72) Inventors: Kevin Kachikian, Los Angeles, CA (US); Briant Benson, Placerville, CA (US)

(73) Assignee: ViruShield, Inc., San Diego, CA (US)

( * ) Notice: Subject to any disclaimer, the term of this patent is extended or adjusted under 35 U.S.C. 154(b) by 482 days.

(21) Appl. No.: 17/105,795

(22) Filed: Nov. 27, 2020

(65) Prior Publication Data

US 2021/0154426 A1 May 27, 2021

Related U.S. Application Data

(60) Provisional application No. 62/941,647, filed on Nov. 27, 2019.

(51) Int. Cl.
| | | |
|---|---|---|
| *A61M 16/06* | (2006.01) | |
| *A61M 16/10* | (2006.01) | |
| *A61M 16/00* | (2006.01) | |

(52) U.S. Cl.
CPC .... *A61M 16/0688* (2014.02); *A61M 16/0003* (2014.02); *A61M 16/107* (2014.02); *A61M 2202/02* (2013.01); *A61M 2205/14* (2013.01); *A61M 2205/18* (2013.01); *A61M 2205/3317* (2013.01); *A61M 2205/3327* (2013.01); *A61M 2205/3331* (2013.01);
(Continued)

(58) Field of Classification Search
CPC . A61M 2202/02; A61M 16/008; A62B 18/00; A62B 9/006
See application file for complete search history.

(56) References Cited

U.S. PATENT DOCUMENTS

| | | | | |
|---|---|---|---|---|
| 2002/0092525 A1* | 7/2002 | Rump | | A62B 9/006 |
| | | | | 128/200.24 |
| 2014/0295605 A1 | 10/2014 | Fedder et al. | | |
| 2019/0009114 A1* | 1/2019 | Han | | A41D 1/002 |

FOREIGN PATENT DOCUMENTS

| | | | |
|---|---|---|---|
| DE | 4002843 C1 | | 4/1991 |
| KR | 20190021971 A | * | 3/2019 |
| WO | 2019172853 A1 | | 9/2019 |

OTHER PUBLICATIONS

WIPO, International Search Report for PCT/US2020/062517, dated Feb. 24, 2021, World Intellectual Property Organization, Geneva, Switzerland.

* cited by examiner

*Primary Examiner* — Samchuan C Yao
*Assistant Examiner* — Tina Zhang
(74) *Attorney, Agent, or Firm* — Temmerman Law; Mathew J. Temmerman

(57) ABSTRACT

A face mask system for detecting gases and volatile organic compounds (VOCs). The face mask system includes a protective mask, at least one communication device, a gas detection device and an external sensor. The gas detection device includes a power supply unit, an inductive coil loop, an internal microcontroller, a wireless communication chip and an internal sensor. The internal sensor is configured to detect and measure a plurality of inside mask VOC readings. The external sensor is configured to detect and measure a plurality of outside mask VOC readings. The external sensor compares an average inside VOC value with an average outside VOC value to provide unique and accurate information of the environment inside the protective mask thereby protecting the user from hazardous situations.

20 Claims, 4 Drawing Sheets

(52) U.S. Cl.
CPC ............... *A61M 2205/3368* (2013.01); *A61M 2205/3553* (2013.01); *A61M 2205/502* (2013.01); *A61M 2205/8206* (2013.01); *A61M 2230/04* (2013.01); *A61M 2230/42* (2013.01)

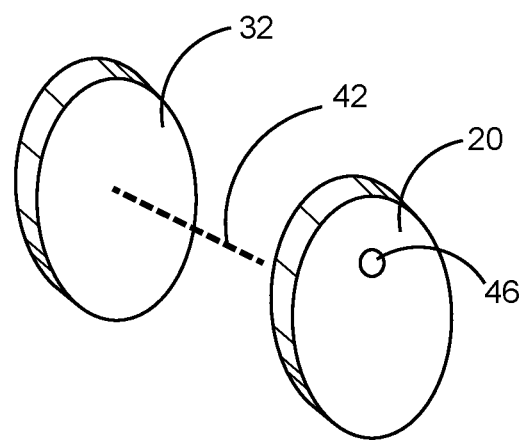
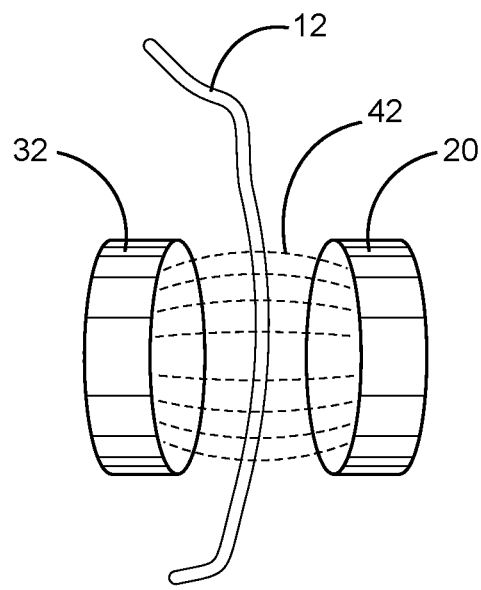
FIG. 3A  FIG. 3B
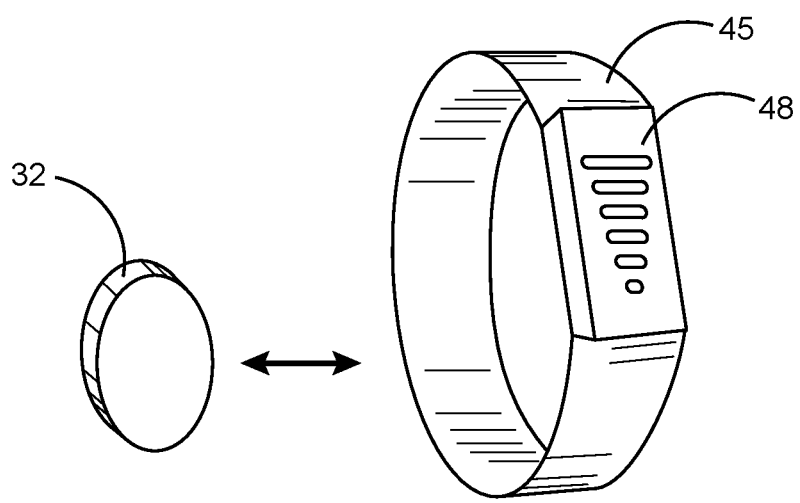
FIG. 4

GAS DETECTOR FOR A FACE MASK

RELATED APPLICATIONS

This application claims priority from the United States provisional application with Ser. No. 62/941,647, which was filed on Nov. 27, 2020. The disclosure of that provisional application is incorporated herein as if set out in full.

BACKGROUND OF THE DISCLOSURE

Technical Field of the Disclosure

The present invention relates generally to face mask systems, and more particularly, to a face mask system featuring a gas detection device for detecting gases and volatile organic compounds (VOCs) thereby providing unique and accurate information of the environment inside a protective mask and protecting the user from hazardous situations.

Description of the Related Art

Face masks are widely utilized as a primary preventive health measure in a community. The face mask acts as an effective barrier in preventing acute respiratory infections and various life-threatening diseases. The face masks are also utilized to protect against polluted air. Gases like carbon monoxide, sulfur dioxide, ozone, lead, nitrogen dioxide and volatile organic compounds (VOCs) cause air pollution. VOCs include artificial and natural chemical compounds which are dangerous to human health. Further, the face masks are widely utilized by workers in fire rescue services, military and chemical industries. Such workplaces are very much confined with low oxygen levels and contain solid and liquid particles including mists, radioactive particles and micro-organisms. Conventional face masks provide limited protection against these hazardous substances.

Several face mask systems have been developed to protect against the aforementioned dangerous situations. One such system describes a mask that substantially covers a wearer's face and includes a peripheral adhesive seal for preventing contaminants from effecting the wearer's visual or respiratory systems. However, this mask system does not detect the presence of VOCs in a working environment. Also, this system is not designed to provide an alert message to a user about any hazardous working environment.

Another face mask system describes a system including an electronics module mounted on an interior of the face mask, wherein the module comprises a pressure sensor, and possibly other sensors, such as gas sensors, temperature sensors, and humidity sensors. This respiratory face mask module is not configured to detect VOCs and does not possess any module for alerting the user about highly polluted environment. Furthermore, a comparison to the internal mask conditions vs. external mask conditions is not contemplated.

Therefore, there is a need for a simple and efficient face mask system for detecting hazardous gases. Furthermore, such a face mask system would detect and measure VOC levels in an environment. Such a system would provide an immediate wireless alert to the user of a potential security breach inside a face mask. Such a system would include sensors for taking continual and random VOC readings to obtain unique and accurate information of the environment inside a protective mask. Further, such a system would inform a manager or a supervisor of a worker wirelessly regarding potentially dangerous working situations. The present embodiment overcomes shortcomings in the field by accomplishing these critical objectives.

SUMMARY OF THE INVENTION

To minimize the limitations found in the prior art, and to minimize other limitations that will be apparent upon the reading of the specification, the present disclosure provides a face mask system for detecting gases and volatile organic compounds (VOCs). The face mask system includes a protective mask, at least one communication device, a gas detection device and an external sensor.

The gas detection device is preferably positioned at an inner portion of the face mask. The gas detection device includes a power supply unit, an inductive coil loop, an internal microcontroller, a wireless communication chip and an internal sensor. The communication device includes a display and an external microcontroller. The communication device is selected from a group consisting of: a cellular telephone, a smartphone, a wireless-enabled personal digital assistant, a tablet, a mobile device and a digital wristband. The power supply unit provides electrical energy to the gas detection device. The inductive coil loop is utilized to recharge the power supply unit. The external microcontroller and the internal microcontroller are programmed with a gas detection application that enables the face mask system to detect gases and VOCs accurately. The wireless communication chip enables the gas detection device and the at least one communication device to communicate wirelessly. The internal sensor is securely positioned at the inner portion of the protective mask and is operatively coupled to the external sensor. The internal sensor is configured to detect and measure a plurality of inside-mask VOC readings. The external sensor is operatively coupled to the communication device. The external sensor detects and measures a plurality of outside mask VOC readings and compares the air quality between inside and outside environment of the mask. The internal and the external sensors are designed to take the VOC readings continually and randomly. The internal microcontroller and the external microcontroller include a VOC calculation module that enables the system to perform various calculations on VOC readings.

The preferred embodiment includes a method for detecting gases and VOCs. The method is initiated by detecting and measuring the plurality of inside mask VOC readings by the internal sensor. Next, the internal microcontroller determines whether at least one of the plurality of inside mask VOC readings exhibits a low VOC value. If the at least one inside mask VOC reading exhibits the low value, then the internal microcontroller determines an average inside VOC value and an absolute inside VOC value. These values are then stored in the internal microcontroller. Thereafter, the average inside VOC value and the absolute inside VOC value are transmitted to the external microcontroller wirelessly. The external sensor detects and measures the plurality of outside mask VOC readings. The external microcontroller receives the average inside VOC value and the absolute inside VOC value from the internal sensor. Next, the external microcontroller calculates an average outside VOC value. The external microcontroller compares the average inside VOC value with the average outside VOC value utilizing the VOC calculation module in the external microcontroller. If the average inside VOC value is greater than or equal to the average outside VOC value, then the external microcontroller sends the alert message regarding a safety breach inside the face mask to the user wirelessly utilizing the at least one communication device. The event in which the average inside VOC value became greater than the average outside VOC value is recorded with related date and time data. Several events of this kind in a short period such as 5 seconds, 30 seconds, 1 minute, 5 minutes, 10 minutes, or 20 minutes trigger the alert message. The comparison between the average inside VOC value and the average outside VOC value provides unique and accurate information of the environment inside the protective mask thereby protecting the user from hazardous situations.

When the internal sensor detects a shallow or no user inhalation, the internal microcontroller sends the alert message to the user and to a base station associated with the face mask system. When the external microcontroller receives the alert message from the internal microcontroller, the external microcontroller displays the alert message on the display of the communication device or notifies the alert message in the form of vibration or an alert sound or notify supervisor of the user wirelessly. The external and internal sensors are designed to detect pressure, temperature, humidity and gases including VOCs from paints, lacquers, paint strippers, cleaning supplies, furnishings, office equipment, glues, adhesives and alcohol. The internal components of the gas detection device are extremely small such that the power supply unit, the microcontroller, the wireless communication chip, the internal sensor and the inductive coil loop can be positioned inside the face mask without breaking a seal member of the mask to the outside world.

In one configuration of the preferred embodiment, the external sensor is mounted on an outer portion of the face mask utilizing a magnetic mount coupled to the internal sensor thereby making the external and the internal sensors magnetically attracted to one another from both the inside and outside of the face mask. In another configuration, the external sensor is mounted on an outer portion of the face mask utilizing an adhesive member such as a double sided tape. In yet another configuration, the external sensor is located at the communication device. Here, data from the internal sensor is transferred to the communication device such as the digital wristband. The wristband display includes a graphical user interface (GUI) that displays information selected from a group consisting of: a comparison between the plurality of inside mask VOC readings and the plurality of outside mask VOC readings, inside and outside humidity and temperature, battery levels, connection status, breath rate and heart rate (obtained from the wristband).

The power supply unit includes at least one battery and associated charging circuitry. When the user wears on his face the protective mask having thereto the gas detection device, the power supply unit senses a movement and enters into an active mode automatically. When the user takes off the mask from the face and either lays the mask down or places the mask on an inductive charger, the power supply unit detects no motion and enters into a sleep mode automatically. In this way, no user interaction is required to turn on or off the gas detection device other than simply removing or wearing the mask.

In certain situations, user's makeup or aftershave could cause the baseline to read higher. In some embodiments this may be compensated for by an acclimation period when the user wears the protective mask for the first time. Therefore, the face mask system is designed to run through a calibration period for achieving a system normalization in every first time the user wears the protective mask. The calibration period may run for a few seconds to a minute or two to enable the face mask system to normalize these undesirable biases.

The face mask system detects differences in VOC readings between the outside environment and the inside mask air and detects timing information about the user's breathing. This timing information is utilized to determine an optimal time to take VOC readings. The plurality of inside mask VOC readings inside the mask accounts for inhalations of the user (low pressure) and the plurality of outside mask VOC readings accounts for exhalations of the user (high pressure).

Information between the internal sensor and the external sensor is transmitted via established communication protocols such as Bluetooth, other wireless communication standards or via magnetic induction so as to allow the transmission of data without breaking the seal member of the mask. Either the internal sensor or both the internal sensor and the external sensor may transmit sensor and other information to an iOS or Android app and/or to the communication device worn on the wrist or in the pocket or around the neck which warns the user of a breach in the internal mask environment.

It is a first objective of the present invention to provide a simple and efficient face mask system for detecting gases and volatile organic compounds (VOCs) in an environment.

A second objective of the present invention is to provide a face mask system that alerts the user of a security breach inside a face mask wirelessly by comparing VOC levels inside and outside of a protective mask.

A third objective of the present invention is to provide a face mask system featuring an automatic power supply unit that does not require any user interaction to turn on and off the system.

A fourth objective of the present invention is to provide a face mask system having internal and external sensors for taking continual and random VOC readings to obtain unique and accurate information of the environment inside a protective mask.

A fifth objective of the present invention is to provide a face mask system that informs a manager or a supervisor of a user wirelessly about a dangerous working situation.

Another objective of the present invention is to provide a face mask system that displays VOC readings on a portable communication device thereby alerting the user instantaneously regarding a safety breach inside the face mask.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention. Thus, the drawings are generalized in form in the interest of clarity and conciseness.

FIG. 3A illustrates a perspective view of the external sensor coupled to an internal sensor utilizing a magnetic mount of the face mask system in accordance with the preferred embodiment of the present invention;

FIG. 3B illustrates a side view of the external sensor coupled to the internal sensor utilizing the magnetic mount shown in FIG. 3A in accordance with the preferred embodiment of the present invention;

FIG. 4 illustrates the internal sensor coupled to a communication device in accordance with the preferred embodiment of the present invention.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term "about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
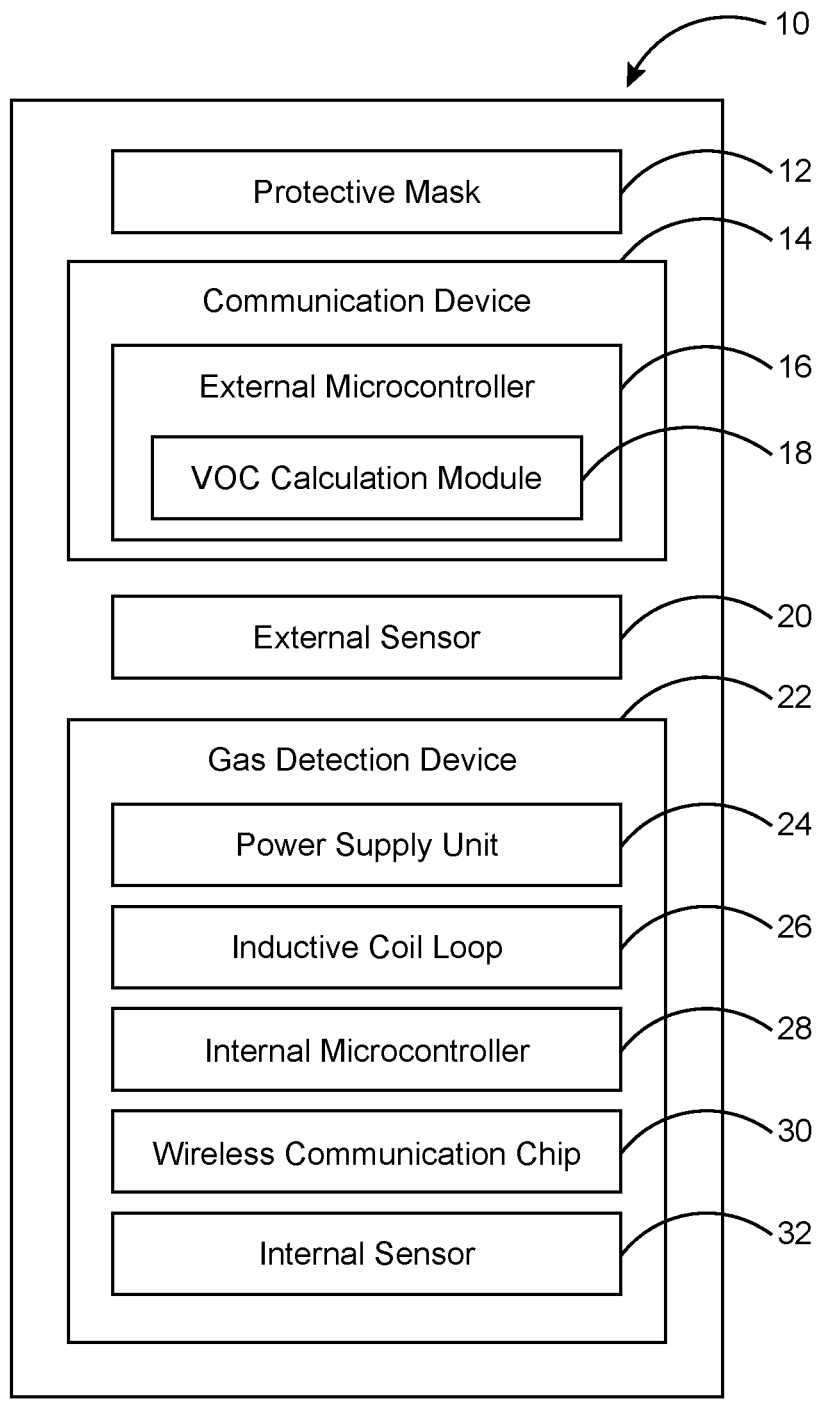
FIG. 1 illustrates a block diagram of a face mask system for detecting gases and volatile organic compounds (VOCs) in accordance with the preferred embodiment of the present invention.
Figure 2:
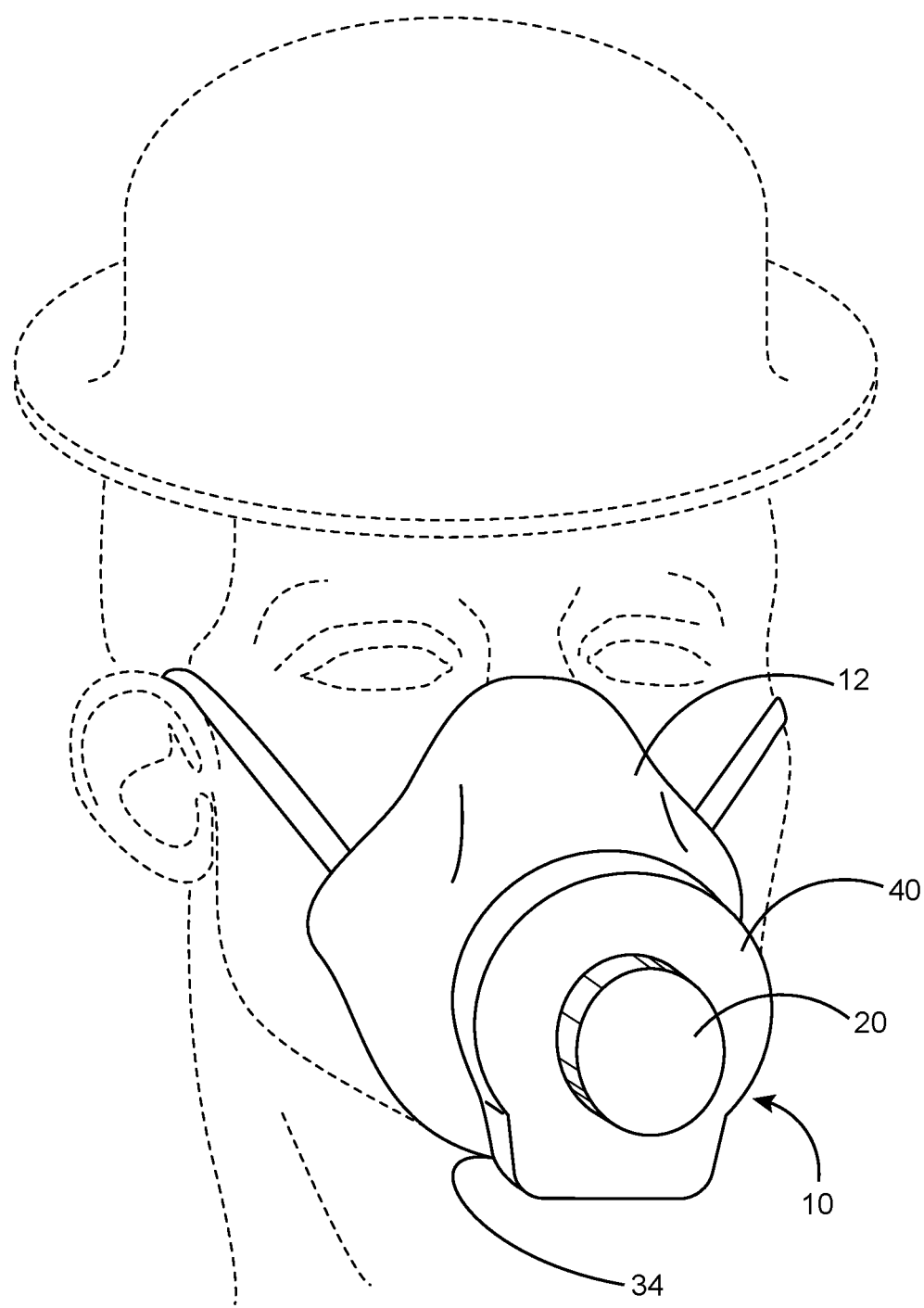
FIG. 2 illustrates a perspective view of an external sensor and a protective mask of a gas detection device of the face mask system in accordance with the preferred embodiment of the present invention.

Referring to FIGS. 1 and 2, a face mask system 10 for detecting gases and volatile organic compounds (VOCs) is illustrated. The face mask system 10 includes a protective mask 12, at least one communication device 14, a gas detection device 22 and an external sensor 20.

The gas detection device 22 is positioned at an inner portion 34 of the protective mask 12. The gas detection device 22 includes a power supply unit 24, an inductive coil loop 26, an internal microcontroller 28, a wireless communication chip 30 and an internal sensor 32. The communication device 14 includes a display 48 (See FIG. 4) and an external microcontroller 16 programmed with a gas detection application. The communication device 14 is selected from a group consisting of: a cellular telephone, a smartphone, a wireless-enabled personal digital assistant, a tablet, a mobile device and a digital wristband 45 (see FIG. 4). The power supply unit 24 provides electrical energy to the gas detection device 22. The inductive coil loop 26 is utilized to recharge the power supply unit 24. The internal microcontroller 28 is programmed with the gas detection application. The wireless communication chip 30 enables the gas detection device 22 and the at least one communication device 14 to communicate wirelessly.

The internal sensor 32 is securely positioned at the inner portion 34 of the protective mask 12. The internal sensor 32 is configured to detect and measure a plurality of inside mask VOC readings. The internal sensor 32 can either attach to the mask 12 internally using a double sided adhesive or it could stick to the user's cheek or lip or elsewhere on the user's face.

The external sensor 20 is operatively coupled to the internal sensor 32 and the at least one communication device 14. The external sensor 20 detects and measures a plurality of outside mask VOC readings and compares the air quality between inside and outside environment of the mask 12. The internal and the external sensors 32, 20 are designed to take the VOC readings continually and randomly. The internal microcontroller 28 and the external microcontroller 16 include a VOC calculation module 18 that enables the system to perform various calculations on the VOC readings.

Figure 5:
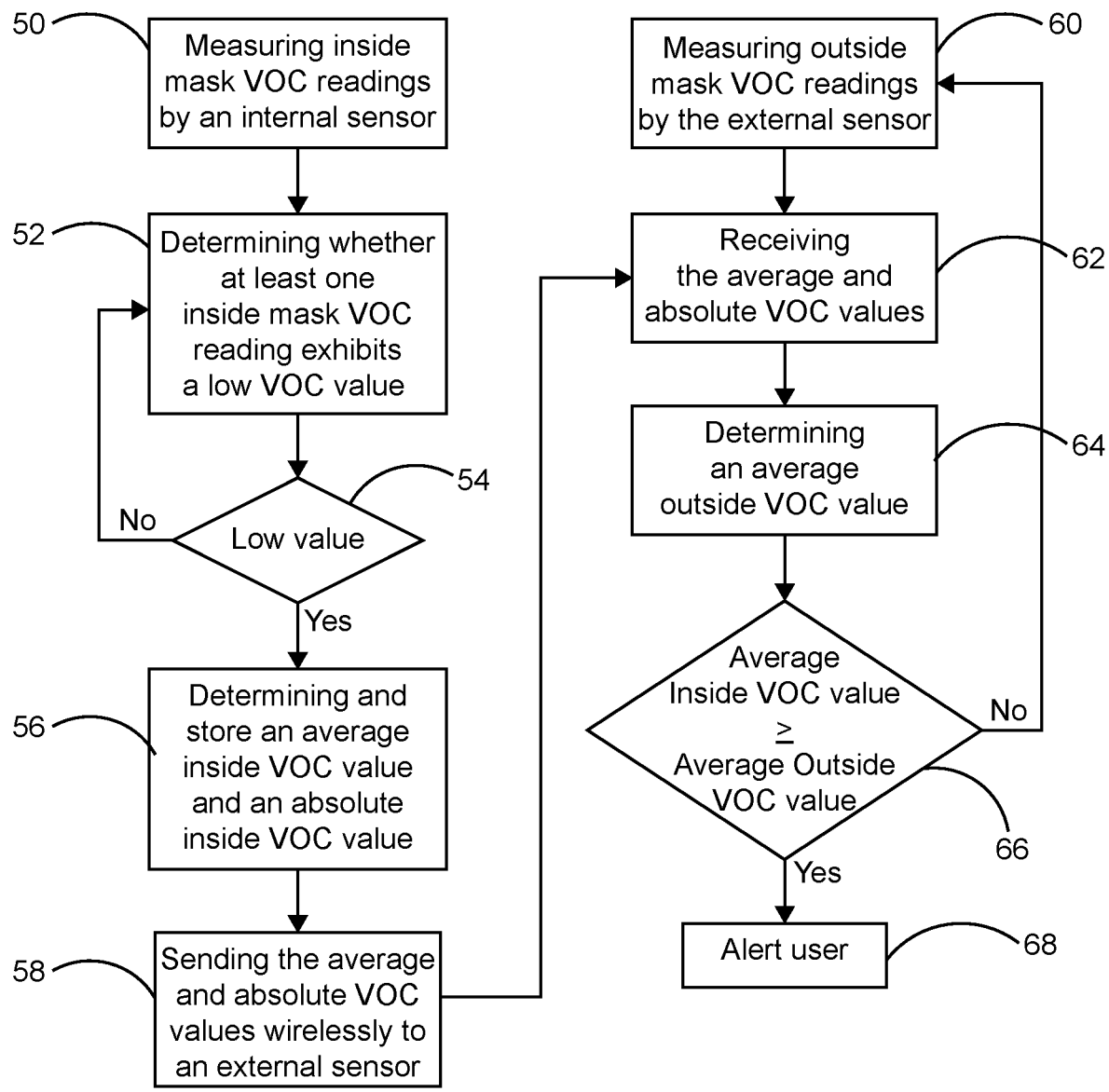
FIG. 5 illustrates a flowchart of a method for detecting gases and VOCs utilizing the face mask system in accordance with the preferred embodiment of the present invention.

FIG. 5 illustrates a flowchart of a method for detecting gases and VOCs utilizing the face mask system 10. The preferred method commences by detecting and measuring the plurality of inside mask VOC readings by the internal sensor as shown in block 50. Next, the internal microcontroller determines if at least one of the plurality of inside mask VOC readings exhibits a low VOC value as shown in block 52. The internal microcontroller checks the value of the at least one inside mask VOC reading as shown in block 54. If the at least one inside mask VOC reading exhibits the low value, then the internal microcontroller determines an average inside VOC value and an absolute inside VOC value as shown in block 56. These values are then stored in the internal microcontroller. If the at least one inside mask VOC reading is not a low value, then the internal microcontroller repeats the check operation to determine if the at least one inside mask VOC reading exhibits a low VOC value. Thereafter, the average inside VOC value and the absolute inside VOC value are transmitted to the external microcontroller wirelessly as indicated at block 58. The external sensor detects and measures the plurality of outside mask VOC readings as shown in block 60. The external microcontroller receives the average inside VOC value and the absolute inside VOC value from the internal sensor as indicated at block 62. Next, the internal microcontroller determines an average outside VOC value as shown in block 64. The external microcontroller compares the average inside VOC value with the average outside VOC value utilizing the VOC calculation module in the external microcontroller as indicated at block 66. If the average inside VOC value is greater than or equal to the average outside VOC value, then the external microcontroller sends the alert message regarding a safety breach inside the face mask to the user wirelessly utilizing the at least one communication device as shown in block 68. If the average inside VOC value is lesser than the average outside VOC value, then the external microcontroller repeats the process of measuring the plurality of outside mask VOC readings. The event in which the average inside VOC value became greater than the average outside VOC value is recorded with date and time in the face mask system 10. Several events of this kind in a short period trigger the alert message. The comparison between the average inside VOC value and the average outside VOC value provides unique and accurate information of the environment inside the protective mask 12 thereby protecting the user from hazardous situations. In an alternate embodiment of the present invention, a pressure sensor is utilized to detect the inhalations and to perform aforementioned calculation process for obtaining accurate information of the environment inside the mask 12.

When the internal sensor 32 detects a shallow or no user inhalation, the internal microcontroller 32 sends the alert message to the user and to a base station associated with the face mask system 10. When the external microcontroller 16 receives the alert message from the internal microcontroller 28, the external microcontroller 16 displays the alert message on the display 48 of the communication device 14 or notifies the alert message in the form of vibration or as an alert sound or notify a supervisor of the user wirelessly.

The external and internal sensors 20, 32 are designed to detect pressure, temperature, humidity and gases including VOCs from paints, lacquers, paint strippers, cleaning supplies, furnishings, office equipment, glues, adhesives and alcohol. The internal components of the gas detection device 22 are extremely small such that the power supply unit 24, the internal microcontroller 28, the wireless communication chip 30, the internal sensor 32 and the inductive coil loop 26 can be positioned inside the mask 12 without breaking a seal member of the mask 12 to the outside world. The external sensor 20 includes a port 46 for receiving at least one electrical cable therethrough.

In one configuration of the preferred embodiment, the external sensor 20 is mounted on an outer portion 40 of the mask 12 utilizing a magnetic mount 42 coupled to the internal sensor 32 thereby making the external and the internal sensors 20, 32 magnetically attracted to one another from either side of the mask 12 as shown in FIGS. 3A and 3B. In another configuration, the external sensor 20 is mounted on the outer portion 40 of the mask 12 utilizing an adhesive member such as a double sided tape. In yet another configuration, the external sensor 20 is located at the at least one communication device 14 as shown in FIG. 4. Here, data from the internal sensor 32 is transferred wirelessly to the communication device 14 such as the digital wristband 45 as shown in FIG. 4. The wristband display 48 includes a graphical user interface (GUI) that displays information selected from a group consisting of: a comparison between the plurality of inside mask VOC readings and the plurality of outside mask VOC readings, inside and outside humidity and temperature, battery levels, connection status, breath rate and heart rate (obtained from the wristband 45). Various parameters such as threshold level and audible warning volume level may be adjustable from the gas detection application or locked by an administrative user.

In one embodiment, the internal sensor 32 and the external sensor 20 are of BME680 by Robert Bosch GmbH of Gerlingen, Germany, although other suitable sensors may be used. Alternatively, these sensors also detect pressure, temperature and humidity. The Bosch sensor currently supplies an Index of Air Quality (IAQ) for a single sensor. Thus, comparing the IAQ of the internal sensor 32 to the IAQ of the external sensor 20 provides unique and accurate information of the environment inside the mask 12 and its relative safety.

The power supply unit 24 includes at least one battery and associated charging circuitry. When the user wears the protective mask 12 with gas detection device 22 on the face, the power supply unit 24 senses movement (breathing is detected from the internal sensor 32) and enters into an active mode automatically. When the user takes off the mask 12 from the face (or when the gas detection device 22 is detached from the mask 12) and either lays the mask 12 down or places the mask 12 on an inductive charger, the power supply unit 24 detects no motion and enters into a sleep mode automatically after a preset amount of time such as 15 or 30 minutes. In this way, no user interaction is required to turn on or off the gas detection device 22 other than simply removing or wearing the mask 12.

In certain situations, user's makeup or aftershave may cause the baseline measurements to read higher even though the user is not in a dangerous environment. In some embodiments this may be compensated for by an acclimation period when the user wears the protective mask 12 for the first time. Therefore, the face mask system 10 is designed to run through a calibration period for achieving a system normalization in every first time the user wears the protective mask 12. The calibration period may run for a few seconds to a minute or two to enable the face mask system to normalize these undesirable biases.

The face mask system 10 detects differences in VOC readings between the outside environment and the inside mask air and detects timing information about the breathing. This timing information is utilized to determine an optimal time to take VOC readings. The plurality of inside mask VOC readings inside the mask 12 accounts for inhalations of the user (low pressure) and the plurality of outside mask VOC readings accounts for exhalations of the user (high pressure). In one embodiment, the inhalations happen through a VOC filter in the face mask which causes a reduction in the VOC readings at that moment but then raise back up temporarily during exhalation. This method allows for the detection of VOC levels outside the mask 12 as compared to true VOC levels inside the mask 12 after having been filtered but before being contaminated by the user's own breath.

As shown in FIG. 4, information between the internal sensor 32 and the communication device 14 is transmitted via established communication protocols such as Bluetooth, other wireless communication standards or via magnetic induction so as to allow the transmission of data without breaking the seal member of the mask 12. Either the internal microcontroller 28 or both the internal microcontroller 28 and the external microcontroller 16 may transmit sensor and other information to an iOS or Android app and/or to the communication device 14 worn on the wrist or in the pocket or around the neck which warns the user of a breach in the internal mask environment. This warning message may be audible, visual, vibrational or a combination of these. The warning message may also be externally transmitted to an outside party or the stationary base station which will then warn other members such as shift supervisors or managers about the breach in the internal mask environment.

In one embodiment, information on a full safety breach inside the mask 12 or simply low air quality may be recorded internally on the gas detection device 22 and is date and time stamped. This information is then transmitted to the base station and recorded for viewing by a manager or for further processing by various data and other record keeping systems. This method provides the ability to check the quality of the seal member of the mask 12 on a day-to-day basis. A long term review and comparison among users in similar environments can be achieved in this method. If a user experiences worse air quality inside the mask 12 than others around or than typically experienced or expected when compared to other external air quality or historical measurement (for instance due to poor mask fitment or uncalibrated sensors), this information may be addressed by a supervisor or simply reported to the user directly.

In yet another configuration of the preferred embodiment, the gas detection device 22 keeps track of data associated with the inside mask VOC readings on a longer term basis such as day-to-day or week-to-week. It is expected that over the life of the mask filter, its filtering capability slowly diminishes over time, and this change can be logged and the life of filter can be predicted utilizing sufficient data available. Based on several recorded patterns of reducing filter capacity over time in a given environment and/or with respect to a given user, a "time to replace" determination may be calculated. This calculation provides the user and any observer of the data, an indication of approximately when the filter should be changed. Once a certain threshold is reached, the system 10 may send an alert to the user that it is time to change the filter.

To further use the data over time, if a certain user happens to equip the mask 12 in a manner that is not adequately sealed, either due to an alignment mismatch, beard, or damage to the mask 12, more outside air than desired may enter the mask 12, and the internal sensor 32 would detect a large short-term change in the level of VOCs during inhalation. This may be reported back to the user or otherwise logged and recorded as data that the user's mask 12 likely needs adjustment.

In an alternative embodiment, the sensor includes or is used in conjunction with an acceleration sensor to detect movement or lack of movement and to detect mask orientation. If the orientation of the mask is horizontal (as compared to the typical vertical position when word by a user standing upright) or if little movement has been detected in a short period or if respiration has been reduced (as calculated by the internal sensor's pressure detector), an alarm may be sent to warn of possible distress. In addition, the accelerometer may record the frequency and duration with which a user lifts his or her mask 12 up away from the face.

In yet another embodiment, a mask 12 includes a head-up display (HUD) that provides internal mask information and/or external mask environment information alongside other relevant information to the wearer. The external mask environment information may be collected either from an external sensor 20 on the mask 12 and/or a wrist worn sensor, and displayed on a face shield of the mask 12 via laser or LED or other standard conventional HUD technologies as is known in the art.

If the air quality of the internal sensor is acceptable and the air quality of the external sensor 20 is acceptable, and the air pressure of both sensors is static, and if the mask is placed in a horizontal position, this would indicate that the mask is not being worn at the moment and the internal circuitry would automatically power down to conserve power. If the mask is in a horizontal position (that is, not being worn) in an environment where both the internal and external sensors 32, 20 are showing high VOC levels, an audible alarm may sound, or an alert may be transmitted to an external data collector.

In certain embodiments, some of the gas sensors require time to warm up before sensor readings reach an adequate level of accuracy. This may in some cases take up to 20 minutes for certain sensors. This lag time between sensor power activation and adequate sensor readings can lead to inefficiencies in the workplace while users await their masks to warm up. In one instance, data is collected regarding the time of day that a user typically lifts his or her mask 12. For example, if a user starts working every morning at 8 AM and equips the mask 12 at that time, this data may be utilized by the system 10, which will learn the pattern and begin initialization early by an amount of time equal to the typical warm-up time for the sensors. In an example, if the sensors typically require 20 minutes to initialize, and the typical time the user dons the mask is 8 am, then the device may begin initialization at 7:40 am such that the mask 12 is ready to go at the expected time it is equipped by the user each day. The system may take into account weekend patterns and not turn itself on early on those days. The system 10 may also power back down on its own if a user does not equip the mask 12 at or near the expected time. If the mask is not sufficiently warmed up, a warning message may be displayed on the wrist-band 45, the HUD, or other device reading and recording data from the mask and/or sensors.

In one embodiment, the battery status information may be transmitted to the iOS/Android app or other external base station. When the battery level reaches a lower threshold level, the user may be notified that battery charging or a batter change is needed. The charging may be accomplished via inductive charging or by simply plugging in the circuitry to a standard USB charger. Since the gas detection device 22 comprises two magnetized portions (or one magnetized and one ferromagnetic), and the masks 12 are typically very thin, one portion of the device 22 may be placed on the inside of the mask 12 and the other portion on the outside. The magnetism between the two draw the two portions toward one another, thereby clamping the thin mask and holding the two portions in place on either side of it. In order to remove and replace the device 22, it is only required to pull the two halves apart and then join the two halves of a second device in their place. The two halves may be joined together directly for storage or charging even where the material of the mask is not fitted between them.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A face mask system comprising:
   a protective mask having an outer portion and an inner portion;
   at least one communication device configured to transmit an alert message to a user, the at least one communication device includes an external microcontroller programmed with a gas detection application;
   a gas detection device positioned at the inner portion of the protective mask to detect gases and volatile organic compounds (VOCs), the gas detection device including:
   a power supply unit to provide electrical energy to the gas detection device;
   an inductive coil loop to recharge the power supply unit;
   an internal microcontroller programmed with a gas detection application;

a wireless communication chip to enable the gas detection device and the at least one communication device to communicate wirelessly; and
an internal sensor to detect and measure a plurality of inside mask VOC readings; and
an external sensor to detect and measure a plurality of outside mask VOC readings;
wherein when at least one of the plurality of inside mask VOC readings exhibits a low VOC value, the internal microcontroller is configured to determine an average inside VOC value and an absolute inside VOC value being transmitted to the external microcontroller wirelessly, the external microcontroller determines an average outside VOC value and compares the average inside VOC value with the average outside VOC value and when the average inside VOC value being greater than the average outside VOC value, the external microcontroller is configured to send the alert message regarding a safety breach inside the face mask to the user wirelessly utilizing the at least one communication device;
whereby the comparison between the average inside VOC value and the average outside VOC value provides information of the environment inside the protective mask thereby protecting the user from hazardous situations.

2. The face mask system of claim 1 wherein the at least one communication device includes a display.

3. The face mask system of claim 2 wherein the internal microcontroller and the external microcontroller include a VOC calculation module that enables the internal and external microcontrollers to calculate average VOC values and to compare the average inside VOC value with the average outside VOC value.

4. The face mask system of claim 2 wherein the display of the at least one communication device includes a graphical user interface (GUI) that displays information selected from a group consisting of: a comparison between the plurality of inside mask VOC readings and the plurality of outside mask VOC readings, inside and outside humidity and temperature, battery levels, connection status, breath rate and heart rate.

5. The face mask system of claim 1 wherein the power supply unit includes at least one battery and associated charging circuitry.

6. The face mask system of claim 1 wherein the power supply unit enters into an active mode automatically when the user wears the protective mask attached with the gas detection device and enters into a sleep mode automatically when the user takes off the mask.

7. The face mask system of claim 1 wherein the external sensor is mounted on the outer portion of the face mask utilizing an adhesive member.

8. The face mask system of claim 1 wherein the external sensor is mounted on the outer portion of the face mask utilizing a magnetic mount coupled to the internal sensor thereby making the external and the internal sensors magnetically attracted to one another from either side of the face mask.

9. The face mask system of claim 1 wherein the external sensor is located at the at least one communication device.

10. The face mask system of claim 1 wherein the internal sensor is securely positioned at the inner portion of the protective mask and is operatively coupled to the external sensor.

11. The face mask system of claim 1 utilizes an initial calibration period for achieving a system normalization when the user first wears the protective mask.

12. The face mask system of claim 1 wherein the plurality of inside mask VOC readings account for low pressure inhalations of the user and the plurality of outside mask VOC readings account for high pressure exhalations of the user.

13. The face mask system of claim 1 wherein the external and internal sensors are designed to detect pressure, temperature, humidity and gases including VOCs from paints, lacquers, paint strippers, cleaning supplies, furnishings, office equipment, glues, adhesives and alcohol.

14. The face mask system of claim 1 wherein the at least one communication device is selected from a group consisting of: a cellular telephone, a smartphone, a wireless-enabled personal digital assistant, a tablet, a mobile device and a digital wristband.

15. The face mask system of claim 1 wherein when the internal sensor detects a shallow or no user inhalation, the internal microcontroller sends the alert message to the user and to a base station associated with the face mask system.

16. The face mask system of claim 1 wherein the protective mask includes a VOC filter that enables the user to inhale safely therethrough.

17. A face mask system comprising:
a protective mask having an outer portion and an inner portion;
at least one communication device configured to transmit an alert message to a user, the at least one communication device includes a display and an external microcontroller programmed with a gas detection application;
a gas detection device positioned inside the protective mask to detect gases and volatile organic compounds (VOCs), the gas detection device including:
a power supply unit to provide electrical energy to the gas detection device;
an inductive coil loop to recharge the power supply unit;
an internal microcontroller programmed with the gas detection application;
a wireless communication chip enables the gas detection device and the at least one communication device to communicate wirelessly; and
an internal sensor securely positioned at the inner portion of the protective mask, the internal sensor being configured to detect and measure a plurality of inside mask VOC readings; and
an external sensor operatively coupled to the internal sensor and the at least one communication device, the external sensor detects and measures a plurality of outside mask VOC readings;
wherein when at least one of the plurality of inside mask VOC readings exhibits a low VOC value, the internal microcontroller is configured to determine an average inside VOC value and an absolute inside VOC value which being transmitted to the external microcontroller, the external microcontroller calculates an average outside VOC value and compares the average inside VOC value with the average outside VOC value utilizing a VOC calculation module in the external microcontroller and when the average inside VOC value being greater than the average outside VOC value, the external microcontroller is configured to send the alert message regarding a safety breach inside the face mask to the user wirelessly utilizing the at least one communication device;

whereby the comparison between the average inside VOC value and the average outside VOC value provides information of the environment inside the protective mask thereby protecting the user from hazardous situations.

18. The face mask system of claim 17 wherein the display of the at least one communication device includes a graphical user interface (GUI) that displays information selected from a group consisting of: a comparison between the plurality of inside mask VOC readings and the plurality of outside mask VOC readings, inside and outside humidity and temperature, battery levels, connection status, breath rate and heart rate.

19. A method for detecting gases and volatile organic compounds (VOCs) utilizing a face mask system, the method comprising:
  a) providing the face mask system having a protective mask, at least one communication device, a gas detection device positioned inside the protective mask and an external sensor operatively coupled to an internal sensor and the at least one communication device;
  b) detecting and measuring a plurality of inside mask VOC readings by the internal sensor;
  c) detecting and measuring a plurality of outside mask VOC readings by the external sensor;
  d) enabling the internal microcontroller to check whether at least one of the plurality of inside mask VOC readings exhibits a low VOC value;
  e) determining an average inside VOC value and an absolute inside VOC value if the at least one of the plurality of inside mask VOC readings exhibits the low VOC value;
  f) transmitting the average inside VOC value and the absolute inside VOC value to the external microcontroller wirelessly;
  g) determining an average outside VOC value by the external microcontroller;
  h) comparing the average inside VOC value with the average outside VOC value by the external microcontroller; and
  i) sending an alert message regarding a safety breach inside the face mask to the user by the external microcontroller wirelessly utilizing the at least one communication device if the average inside VOC value being greater than the average outside VOC value;

whereby the comparison between the average inside VOC value and the average outside VOC value provides information of the environment inside the protective mask thereby protecting the user from hazardous situations.

20. The method of claim 19 wherein the at least one communication device includes a display having a graphical user interface (GUI) that displays information selected from a group consisting of: a comparison between the plurality of inside mask VOC readings and the plurality of outside mask VOC readings, inside and outside humidity and temperature, battery levels, connection status, breath rate and heart rate.

* * * * *